United States Patent [19]

Kim et al.

[11] Patent Number: 5,424,468
[45] Date of Patent: Jun. 13, 1995

[54] POLYMERIC CONTACT LENS MATERIAL OF IMPROVED OXYGEN PERMEABILITY

[75] Inventors: Kwang U. Kim; Tae S. Park; Seung S. Hwang; Jong C. Lee, all of Seoul; Moo S. Lee, Kyonggi-do; Seong M. Cheong, Seoul, all of Rep. of Korea

[73] Assignee: Korea Institute of Science and Technology, Seoul, Rep. of Korea

[21] Appl. No.: 189,607

[22] Filed: Feb. 1, 1994

[51] Int. Cl.$^6$ .................. C08F 18/20; C08F 214/18
[52] U.S. Cl. .................... 554/226; 554/42; 554/43; 554/44; 554/223; 554/224; 554/225; 526/245; 526/279; 523/108; 525/326.2
[58] Field of Search .............. 554/226, 42, 43, 44, 554/223, 224, 225; 526/245, 279; 523/108; 525/326.2

[56] References Cited

U.S. PATENT DOCUMENTS

| | | | |
|---|---|---|---|
| 3,619,044 | 11/1971 | Kamath | 351/160 |
| 3,984,485 | 10/1976 | Neefe | 260/63 UY |
| 4,182,822 | 1/1980 | Chang | 526/264 |
| 4,284,749 | 8/1981 | Neefe | 526/304 |
| 4,330,383 | 5/1982 | Ellis et al. | 526/304 |
| 4,424,328 | 1/1984 | Ellis | 526/279 |
| 4,433,111 | 2/1984 | Tighe et al. | 525/326.2 |
| 4,493,910 | 1/1985 | Tighe et al. | 523/108 |
| 4,540,761 | 9/1985 | Kawamura et al. | 526/245 |
| 4,604,479 | 8/1986 | Ellis | 556/440 |
| 4,686,267 | 8/1987 | Ellis et al. | 556/440 |
| 4,826,936 | 5/1989 | Ellis | 526/245 |
| 4,990,582 | 2/1991 | Salamone | 526/245 |
| 5,010,141 | 4/1991 | Mueller | 525/276 |
| 5,032,641 | 7/1991 | Nanishi et al. | 524/544 |
| 5,057,585 | 10/1991 | Agou et al. | 526/246 |
| 5,115,056 | 5/1992 | Mueller et al. | 526/243 |
| 5,162,391 | 11/1992 | Ikari | 523/107 |
| 5,162,469 | 11/1992 | Chen | 526/245 |

OTHER PUBLICATIONS

Journal of Fluorine Chemistry, No. 43, pp. 277–290, Jan. 23, 1989, H. W. Prokop, et al., "Analysis of the Products from the Electrochemical Fluorination of Octanoyl Chloride".

*Primary Examiner*—Arthur C. Prescott
*Attorney, Agent, or Firm*—Oblon, Spivak, McClelland, Maier, & Neustadt

[57] ABSTRACT

This specification provides a polymeric material useful for manufacturing contact lenses having improved oxygen permeability. The contact lenses prepared from the polymeric material of the invention show improved hydrophilicity and enhanced oxygen permeability as compared with that made of the conventional fluoroalkyl-containing polymeric materials.

11 Claims, No Drawings

POLYMERIC CONTACT LENS MATERIAL OF IMPROVED OXYGEN PERMEABILITY

BACKGROUND OF THE INVENTION

1. Field of the Invention

The present invention relates to a polymeric contact lens material of improved oxygen permeability. More particularly, the present invention relates to a fluoroalkyl-containing monomer and a polymeric composition containing the monomer, which is useful as a contact lens material.

2. Description of the Prior Art

It is known that contact lenses may be made of polymethylmethacrylate (PMMA). This material is not harmful to the human body and shows good optical permeability. However, the contact lenses made of the PMMA may interfere the metabolism of the eyes when worn for a long time because of the properties of the material such as high stiffness and low oxygen permeability.

In order to solve these problems, intensive researches have been made. For example, a method has been suggested which comprises copolymerizing a siloxanyl alkyl ester of methacrylic acid with an acrylic monomer to obtain a polymer having enhanced oxygen permeability. Such improved oxygen permeability is considered to be attributed to the high oxygen-solubility of the siloxane group contained in the resulting polymer. The representative examples of this method are described in U.S. Pat. Nos. 4,330,383; 4,491,905; 4,424,328; 4,463,149; 4,535,138; 4,826,936; 4,826,889; 4,769,431; 4,625,007; 4,604,479; 4,582,884; and 4,535,138.

Other methods have been proposed in U.S. Pat. Nos. 4,996,275; 4,686,267; and 4,661,573, which comprises copolymerizing a silicone-containing monomer with an acrylic monomer. In accordance with this method, oxygen permeability can be increased by increasing the amount of the silicone-containing monomer to be copolymerized. In this method, an increased amount of the silicone-containing monomer may result in the degradation of ocular biocompatibility because the monomer reduces the processing ability of the resulting polymer and renders the polymer highly hydrophobic.

U.S. Pat. No. 4,990,582 proposes a method of preparing a contact lens material of improved oxygen permeability, wherein a fluorine-containing monomer is used. This type of the monomer is capable of providing the oxygen permeability, the silicone-containing monomer, without decreasing the processing ability significantly. However, this method suffers from the degraded the ocular biocompatibility of the resulting polymer. In other words, the larger the content of fluorine is, the higher the hydrophobicity is, even though the oxygen permeability is improved. Since the most of the fluorine-containing monomers are made by esterifying acrylic acid, methacrylic acid or itaconic acid with a fluoroalkyl alcohol, they have only one ester group per fluoroalkyl as a hydrophilic group. This is the reason why such fluorine-containing monomers have a lower concentration of the hydrophilic group.

An attempt has been made to improve biocompatibility of the homopolymers of either silicone-containing monomers or fluorine-containing monomers, or the copolymer thereof. For example, U.S. Pat. No. 3,619,044 suggests to introduce a number of hydrophilic groups into the surface of the contact lenses. However, this method suffers from the defects that the transparency of the lenses decreases significantly with the lapse of their wearing time, because the proteins contained in tears are deposited on the surface of the lenses.

SUMMARY OF THE INVENTION

It is therefore an object of the invention to provide a polymeric material for producing contact lenses which can eliminate the disadvantages encountered in the prior art techniques.

It is another object of the invention to provide a novel fluoroalkyl-containing monomer which can impart a high level of hydrophilicity to the resulting polymer for contact lenses.

It is still another object of the invention to provide a homopolymer of the fluoroalkyl-containing monomer according to the invention.

It is still further object of the invention to provide a polymeric composition containing the fluoroalkyl-containing monomer according to the invention, which enables ones to produce contact lenses of improved hydrophilicity and enhanced oxygen permeability.

Further objects of the invention will become apparent through reading the remainder of the specification.

DETAILED DESCRIPTION OF THE INVENTION

We, the inventors of the present invention, unexpectedly discovered that a monomer containing two ester or ethersulfonyl groups or a hydrophilic group of the formula:—CONHCO—, —CON(CO)$_2$—, —CONHSO$_2$—, or —CON(SO$_2$)$_2$—, as hydrophilic groups per molecule can enhance the hydrophilicity of the resulting polymer, as compared with the conventional fluorine-containing monomers.

The fluoroalkyl-containing monomer according to the invention is prepared by reacting a fluoroalkyl carboxylic acid, a fluoroalkyl carboxyl halide, a fluoroalkyl sulfonic acid, or a fluoroalkyl sulfonyl halide with an acrylic monomer containing either a hydroxyl group or an amine group, an acrylic monomer containing both a hydroxyl group and an amine group, a styrene monomer containing a hydroxyl group or an amine group, or a vinylether monomer containing a hydroxyl group. The homopolymers or copolymers of the fluoroalkyl-containing monomer of the invention show high oxygen permeability.

The reaction of a carboxylic acid or a sulfonic acid with a hydroxyl group or an amine group is known in literatures. See, "*Tetrahedron*", Vol. 21, p. 3531 (1965); "*Am. Soc.*", Vol. 81, p. 890 (1949); "*Org. Syn.*," Coll. Vol 1, p. 110 (1955); and "*Synthesis,*" p.429 (1979). A reaction of a carboxyl halide or sulfonyl halide with a hydroxyl group or an amine group is also known. See, "*Org. Syn. Coll.,*" Vol 3, p. 366 (1955); "*J. of Fluorine Chemistry,*" Vol. 20,p. 515 (1982); "*Chemical Society Journal,*" p. 2640 (1957); "*Reagents for Organic Synthesis,*" Vol. 1, p. 662; "*J. Org.,*" Vol. 26, p. 225 (1961); and "*Org. Prep. Proc.,*" Vol. 1, p. 255 (1969).

However, it has not been known prior to the invention that a fluoroalkyl-containing monomer which is useful for contact lenses having enhanced oxygen permeability can be prepared by reacting a fluoroalkyl carboxylic acid, a fluoroalkyl carboxyl halide, a fluoroalkyl sulfonic acid, or a fluoroalkyl sulfonyl halide with an acrylic monomer containing a hydroxyl group or an amine group, an acrylic monomer containing both a hydroxyl group and an amine group, a styrene monomer containing a hydroxyl group or an amine group, or a vinylether monomer containing a hydroxyl group.

Therefore, in an aspect of the invention, a fluoroalkyl-containing monomer is provided which has two ester or ethersulfonyl group or a hydrophilic group of the formula: —CONHCO—, —CON(CO)$_2$—, —CONHSO$_2$—, or —CON(SO$_2$)$_2$—, as hydrophilic groups per molecule.

The fluoroalkyl carboxylic acid which can be used in the invention is represented by the following formula:

R—(C=O)OH wherein R is a straght, branched or cyclic alkyl having 1 to 20 carbon atoms and 1 to 41 fluorine atoms, or a phenyl containing 1 to 5 fluorine atoms.

The fluoroalkyl carboxyl halide includes a compound represented by the following formula:

R—(C=O)X wherein R is a straght, branched or cyclic alkyl having 1 to 20 carbon atoms and 1 to 41 fluorine atoms, or a phenyl containing 1 to 5 fluorine atoms; and X is a fluorine, chlorine, bromine, or iodine atom. The fluoroalkyl sulfonic acid includes a compound represented by the following formula:

R—(O=S=O)OH wherein R is a straght, branched or cyclic alkyl having 1 to 20 carbon atoms and 1 to 41 fluorine atoms, or a phenyl containing 1 to 5 fluorine atoms.

The fluoroalkyl sulfonyl halide includes a compound represented by the following formula:

R—(O=S=O)X wherein R is a straght, branched or cyclic alkyl having 1 to 20 carbon atoms and 1 to 41 fluorine atoms, or a phenyl containing 1 to 5 fluorine atoms; and X is a fluorine, chlorine, bromine, or iodine atom.

Although any acrylic monomers having a hydroxyl group and a radical-polymerizable acrylic group can be used in the invention, the preferred examples include an acrylic monomer of the following formula:

$$CH_2=C-R^1 \atop {\underset{O-(CH_2)_n-OH}{\overset{|}{C=O}}}$$ (I)

wherein $R^1$ is hydrogen, or $CH_3$ or —$CH_2(C=O)O(CH_2)_nOH$; and n is an integer of 1 to 6; in particular, 2-hydroxy-3-chloropropyl acrylate, 2-hydroxy-3-chloropropyl methacrylate and the like.

The acrylic monomers containing an amine group employed herein may be those having an amine group and a radical-polymerizable acrylic group. The preferred example of such monomers is represented by the formula:

$$CH_2=C-R^2 \atop {\underset{H-N-R^3}{\overset{|}{C=O}}}$$ (II)

wherein $R^2$ is hydrogen, or $CH_3$ or —$CH_2(C=O)NHR^3$; and $R^3$ is a hydrogen atom or an alkyl having 1 to 6 carbon atoms.

The acrylic monomers containing both a hydroxyl group and an amine group employed herein may be all compounds having a hydroxyl group and an amine group, and a radical-polymerizable acrylic group. That is, such compounds include, for example, N-2-hydroxylethyl acrylamide, N-2-hydroxyethylmethacrylate, p-hydroxylphenyl acrylamide, p-hydroxylphenyl methacrylamide, N-methylol acrylamide, and N-methylol methacrylamide.

As an exemple of the styrene monomers containing a hydroxyl group employed herein, 4-hydroxymethylstyrene or 4-hydroxystyrene can be mentioned. The representative example of the styrene monomer containing an amine group includes 4-aminostyrene. The vinyl ether monomers containing a hydroxyl group includes hydroxybutyl vinyl ether.

In another aspect of the invention, a contact lens material of high oxygen premeability and good ocular compatibility is provided which comprises a homopolymer of the fluoroalkyl-containing monomers according to the invention.

In further aspect of the invention, a polymeric composition is provided which can produce the desired contact lenses of improved oxygen permeability and enhanced hydrophilicity. The transparency of the resulting lenses is not deteriorated as the lapse of its wearing time. The polymeric composition according to the invention comprises:

a) 5 to 100 wt % of a fluoroalkyl-containing monomer;
b) 0 to 60 wt % of a silicone-containing monomer;
c) 0 to 60 wt % of a vinyl monomer;
d) 0 to 10 wt % of a cross-linking monomer; and
e) 0 to 5 wt % of a hydrophilic monomer.

As fully discussed above, the fluoroalkyl-containing monomer a) contains two ester or ethersulfonyl groups or a hydrophilic group of the formula: —CONHCO—, —CON(CO)$_2$—, —CONHSO$_2$—, or —CON(SO$_2$)$_2$—, as hydrophilic groups per molecule.

The silicone-containing monomer b), which is used as a component of the polymeric compositions according to the invention, may be include those monomers disclosed in U.S. Pat. Nos. 4,330,383; 4,491,905; 4,424,328; 4,463,149; 4,k535,138; 4,826,936; 4,826,889; 4,769,431; 4,625,007; 4,604,479; 4,582,884; 4,535,138; and 4,686,267; and may be represented by the formula:

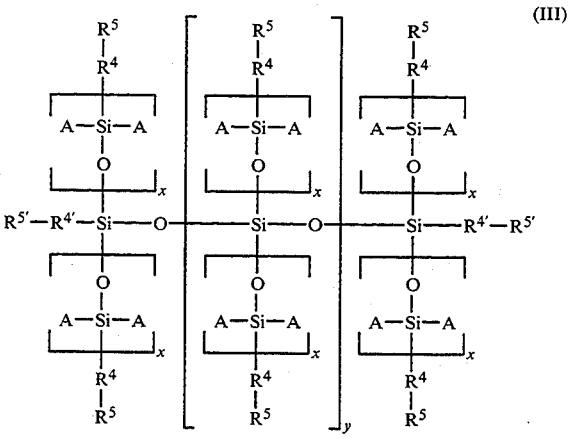

wherein $R^{5'}$ is a polymerizable, unsaturated group; $R^{4'}$ is a divalent hydrocarbonyl group having 1 to 10 carbon atoms; $R^5$ is a hydrogen atom or a polymerizable, unsaturated group; $R^4$ is a divalent hydrocarbonyl group having 1 to 10 carbon atoms, or phenyl; A is a straight, branched or cyclic alkyl group having 1 to 5 carbon atoms which is further substituted with a phenyl group and the group Z, wherein Z is selected from the group consisting of trimethylsiloxy, pentamethyldisiloxanyl, heptamethyltrisiloxanyl, nonamethyltetrasiloxanyl, bis(trimethylsiloxy)methylsiloxanyl, and tris(trimethylsiloxy)siloxanyl; x is an integer of 0 to 10, provided that the sum of x is at least 2; and y is an integer of 0 to 10.

The examples of the vinyl monomer c) may include an acrylic monomer of the formula:

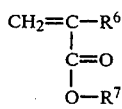

(IV)

wherein $R^6$ is a hydrogen atom, or $CH_3$ or $-CH_2(-C=O)OR^7$; and $R^7$ is a hydrocarbonyl group having 1 to 20 carbon atoms, or styrene or alpha-methyl styrene group.

The cross-linked monomer d) may include ethyleneglycol dimethacrylate, diethyleneglycol dimethacrylate, tetraethyleneglycol dimethacrylate, trimethylolpropane triacrylate, glycerol trimethacrylate, and divinyl benzene.

The hydrophilic monomer e) may include acrylic acid, methacrylic acid, N-2-hydroxyethyl acrylamide, N-2-hydroxyethyl methacrylamide, N-methylol acrylamide, N-methylol methacrylamide, and N-vinylpyrrolidone as well as the monomers of the formulae (I) and (II) defined above.

PREFERRED EMBODIMENT OF THE INVENTION

The invention will be illustrated in greater detail by way of the following examples. The examples are presented for illustrative purposes only and should not be considered as limiting the scope of the invention, which is properly delineated in the claims.

EXAMPLE 1

Preparation of 2-Perfluorooctanecarboxylethyl Methacrylate ("CEMA")

To a 1 l reactor equipped with a reflux condenser, a temperature controller and a stirrer, 130.15 g of hydroxyethyl methacrylate was added and the resulting mixture maintained below 5° C. To this mixture, [***] g of hydroxyethyl methacrylate was added and heated at 50° C. Into the reactor, 482.6 g of molten perfluorooctanecarboxylic chloride was introduced slowly. At this time, the reaction temperature was adjusted not to exceed 10° C. After removing the resulting hydrogen chloride as a by-product, the reaction mixture was distilled in vacuum to give 530 g of CEMA. B.P.: 58° C. at $10^{-6}$ mmHg.

EXAMPLE 2

Reparation of 2-Perfluorooctane Carboxyethyl Methacrylate

To a 1 l reactor equipped with a reflux condenser, a temperature controller and a stirrer, 500 ml of dichloromethane, 65.075 g of hydroxyethyl methacrylate, and 241.3 g of perfluorooctane carboxylic acid were added. The resulting mixture was stirred with maintaining the reaction temperature at 25° C. To the stirred mixture, 206 g of N,N'-dicyclohexyl-carbodiimide was added slowly at the same temperature. The reaction was continued for 24 hours with stirring. A fractional distillation gave 184 g of CEMA. B.P.: 58° C. at $10^{-6}$ mmHg.

EXAMPLE 3

Preparation of N-Perfluorooctanesulfonyl Acrylamide ("SAAm")

To a 1 l reactor equipped with a reflux condenser, a temperature controller and a stirrer, 150 ml of dichloromethane and 35.54 g of acrylamide were added to give a homogeneous solution, which was then maintained at 10° C. While maintaining the reactor at 10° C., a solution of 259.3 g of perfluorooctanesulfonyl chloride in 350 ml of dichloromethane, and the resulting solution introduced slowly into the reactor. After removing dichloromethane under reduced pressure, the resulting SAAm was recrystallized from acetone to yield 260 g of pure SAAm. B.P.: 30° C.

A set of contact lenses prepared from the polymeric compositions obtained in Examples 4 to 9 and Comparative Examples 1 to 5 were put to test with respect to the oxygen permeability invention was measured using a Rikaseiki gas permeability tester (model K-316 IPI available from Rikaseiki Incorporated, Japan) at 35° C. in accordance with the polarography method [See: R. W. W. Stevenson and R. O. Ansell, "The Reliability of Polaragraphic Oxygen Measurements Across Gas Permeable Contact Lenses," the CLAO Journal, vol 17(1), (1991)]. The oxygen permeability was evaluated in the following unit: $10^{-11}$ $cm^3.cm/cm^2.s.mmHg$.

The hyrophilicity of the resulting contact lens was determined by dropping a several drops of an isotonic salic solution onto the contact lens in the form of a plate having a thickness of 1 mm, and measuring the contact angles formed between the salic solution drops and the surface of the plate at 25° C. This test was carried out by using a measuring instrument, Model G-I (available from Erma Inc., Japan).

The oxygen permeability and the hydrophilicity data determined above are listed in Table 1 below.

TABLE 1

| Component | Examples | | | | | | Comparative Examples | | | | |
|---|---|---|---|---|---|---|---|---|---|---|---|
| | Ex. 4 | Ex. 5 | Ex. 6 | Ex. 7 | Ex. 8 | Ex. 9 | C. Ex. 1 | C. Ex. 2 | C. Ex. 3 | C. Ex. 4 | C. Ex. 5 |
| MMA | 5 | 15 | 15 | 15 | 15 | 15 | 83 | 83 | 83 | 83 | 83 |
| Si monomer | 40 | 40 | 40 | 40 | 40 | 40 | 12 | 12 | 12 | 12 | 12 |
| EC-4 | 3 | 3 | 3 | 3 | 3 | 3 | | | | | |
| MAA | 2 | 2 | 2 | 2 | 2 | 2 | | | | | 5 |
| PFOMA | | | | | | | 5 | | | | |
| CEMA | 20 | 40 | | | | | | 5 | | | |
| SAAm | 20 | 40 | | | | | | | | | |
| CMS | | | 40 | | | | | | | 5 | |
| CIms | | | | 40 | | | | | | | |

TABLE 1-continued

| Component | Examples | | | | | | Comparative Examples | | | | |
|---|---|---|---|---|---|---|---|---|---|---|---|
| | Ex. 4 | Ex. 5 | Ex. 6 | Ex. 7 | Ex. 8 | Ex. 9 | C. Ex. 1 | C. Ex. 2 | C. Ex. 3 | C. Ex. 4 | C. Ex. 5 |
| CBVE | | | | | | 40 | | | | | |
| oxygen permeability | 89.2 | 78.8 | 82.2 | 76.3 | 80.3 | 77.4 | 2.9 | 8.9 | 4.5 | 6.5 | 2.4 |
| contact angles | 62.3 | 68.9 | 69.3 | 70.2 | 72.1 | 72.1 | 70.2 | 65.3 | 68.7 | 72.4 | 58.6 |

MMA: methyl methacrylate
Si monomer: 3-methacryloxypropyltris(trimethylsiloxy)silane
ED-4: tetraethylene glycol diacrylate
MAA: methacrylic acid
PFOMA: perfluorooctylmethacrylate
CEMA: 2-perfluorooctanecarboxyethyl
SAAm: 4-perfluorooctanesulfonyl acrylamide
CMS: 4-perfluorooctanecarboxymethyl styrene
CImS: 4-perfluorooctanecarboxyiminostyrene
CBVE: 4-perfluorooctanecarboxybuthylvinylether
Polymerization conditions: AIVN[2,2'-azovis(2,4-dimethyl-valeronitrile)]0.003 wt %, 60° C., 48 hrs.

What is claimed is:

1. A fluoroalkyl-containing monomer containing two hydrophilic ester or ethersulfonyl groups, or a hydrophilic group of the formula: —CONHCO—, —CON(-CO)$_2$—, —CONHSO$_2$— or —CON(SO$_2$)$_2$— per molecule, said monomer being prepared by reacting a fluoroalkyl carboxylic acid, a fluoroalkyl carboxyl halide, a fluoroalkyl sulfonic acid, or a fluoroalkyl sulfonyl halide with an acrylic monomer containing a hydroxyl or an amine group, an acrylic monomer containing a hydroxyl and an amine group, a styrene monomer containing a hydroxyl or amine group, or a vinylether monomer containing hydroxyl group.

2. The monomer as claimed in claim 1, wherein the fluoroalkyl carboxylic acid is represented by the formula:

R—(C=O)OH wherein R is a straght, branched or cyclic alkyl having 1 to 20 carbon atoms and 1 to 41 fluorine atoms, or phenyl containing 1 to 5 fluorine atoms.

3. The monomer as claimed in claim 1, wherein the fluoroalkyl carboxyl halide is represented by the formula:

R—(C=O)X wherein R is a straght, branched or cyclic alkyl having 1 to 20 carbon atoms and 1 to 41 fluorine atoms, or phenyl containing 1 to 5 fluorine atoms; and X is a fluorine, chlorine, bromine, or iodine atom.

4. The monomer as claimed in claim 1, wherein the fluoroalkyl sulfonic acid is represented by the formula:

R—(O=S=O)OH wherein R is a straght, branched or cyclic alkyl having 1 to 20 carbon atoms and 1 to 41 fluorine atoms, or phenyl containing 1 to 5 fluorine atoms.

5. The monomer as claimed in claim 1, wherein the fluoroalkyl sulfonyl halide is represented by the formula:

R—(O=S=O)X wherein R is a straght, branched or cyclic alkyl having 1 to 20 carbon atoms and 1 to 41 fluorine atoms, or phenyl containing 1 to 5 fluorine atoms; and X is a fluorine, chlorine, bromine, or iodine atom.

6. The monomer as claimed in claim 1, wherein the acrylic monomer is a compound of the formula:

$$\begin{array}{c} CH_2=C-R^1 \\ | \\ C=O \\ | \\ O-(CH_2)_n-OH \end{array} \quad (I)$$

wherein, $R^1$ is hydrogen, or $CH_3$ or —$CH_2(-C=O)O(CH_2)_nOH$; n is an integer of 1 to 6; or 2-hydroxy-3-chloropropyl acrylate or 2-hydroxy-3-chloropropyl methacrylate.

7. The monomer as claimed in claim 1, wherein the acrylic monomer containing an amine group is represented by the formula:

$$\begin{array}{c} CH_2=C-R^2 \\ | \\ C=O \\ | \\ H-N-R^3 \end{array} \quad (II)$$

wherein $R^2$ is hydrogen, or $CH_3$ or —$CH_2(-C=O)NHR^3$, $R^3$ is a hydrogen atom or an alkyl having 1 to 6 carbon atoms.

8. The monomer as claimed in claim 1, wherein the acrylic monomer containing a hydroxyl group and an amine group is selected from the group consisting of N-2-hydroxyethyl acrylamide, N-2-hydroxyethyl methacrylamide, p-hydroxyphenyl acrylamide, p-hydroxyphenyl methacrylamide, N-methylol acrylamide, and N-methylolmethacrylamide.

9. The monomer as claimed in claim 1, wherein the styrene monomer containing hydroxyl group is 4-hydroxymethyl styrene or 4-hydroxy styrene.

10. The monomer as claimed in claim 1, wherein the vinylether monomer containing a hydroxyl group is hydroxybutyl vinyl ether.

11. The monomer as claimed in claim 1, wherein the styrene monomer containing an amine group are 4-amino styrene.

* * * * *